United States Patent [19]

Brooks

[11] Patent Number: 4,632,097
[45] Date of Patent: Dec. 30, 1986

[54] KNEE BRACE

[76] Inventor: Richard R. Brooks, 9160 Shanley La., Auburn, Calif. 95603

[21] Appl. No.: 733,091

[22] Filed: May 13, 1985

[51] Int. Cl.$^4$ .................................................. A61F 3/00
[52] U.S. Cl. ..................................... 128/80 C; 128/88; 2/24
[58] Field of Search ............... 128/80 C, 88, 87, 80 R, 128/80 F, 80 H; 2/23, 24

[56]  References Cited

U.S. PATENT DOCUMENTS

| | | | |
|---|---|---|---|
| 2,460,895 | 2/1949 | Meany | 128/88 |
| 3,669,105 | 6/1972 | Castiglia | 128/80 C |
| 4,249,524 | 2/1981 | Anderson | 128/80 C |
| 4,323,059 | 5/1982 | Ronbert | 128/80 C |
| 4,493,316 | 1/1985 | Reed et al. | 128/88 |

FOREIGN PATENT DOCUMENTS

| | | | |
|---|---|---|---|
| 2472375 | 7/1981 | France | 128/88 |
| 105419 | 5/1917 | United Kingdom | 128/88 |

*Primary Examiner*—Gene Mancene
*Assistant Examiner*—John G. Weiss
*Attorney, Agent, or Firm*—Mark C. Jacobs

[57] ABSTRACT

A knee stabilizer comprised of 2 spaced plates, one of which has an exterior portion extending linearly in the direction of the second plate, the plates each having a pulley with a fixed release mantel on the top side of the pulleys, the pulleys carrying a rigid endless belt on the sheaves thereof. The underside of the plates carry either a rubber layer or a layer of one side of a Velcro brand fastener system.

11 Claims, 9 Drawing Figures

KNEE BRACE

BACKGROUND OF THE INVENTION

Many previously used knee braces comprise simple hinged structures that, while capable of some pivoting, cannot move parallel to and with the motion of the knee joint. Some of these devices also fail to provide protection to injured knee ligaments.

U.S. Pat. No. 4,249,524 issued in 1981 to George Anderson solved many of the prior art problems. Yet some of these remained until the present invention.

Thus it is an object of this invention to provide an improved knee stabilizer device.

Another object is to provide a device that can be used easily by athletes and others to protect their knees from injury.

It is a further object to provide a knee stabilizer capable of instantaneous lockup on impact while affording full movement flexibility during normal use of the knee area.

Yet another object is to provide a knee area brace adapted to prevent injury to the knee comprising a pair of interconnected arcuate pressure pads.

These and other objects of the invention will in part be obvious and will in part appear hereinafter.

The invention accordingly comprises the product possessing the features, properties and the relation of elements which are exemplified in the following detailed disclosure, and the scope of the application of which will be indicated in the claims.

For a fuller understanding of the nature and objects of the invention, reference should be had to the following detailed description taken in connection with the accompanying drawing.

SUMMARY OF THE INVENTION

The knee stabilizer of this invention constitutes a pair of arcuate plates spaced from each other, each of which has a pulley mounted on the top surface thereof, said pulleys carrying a rigid endless belt which can lock up rigidly upon the application of pressure to the area adjacent to the kneecap, either above or below same, and which endless belt will relax on the relief of the pressure.

Two embodiments are disclosed the first of which is bound to the leg by adhesive tape, the second of which includes a wrap that is rotated around the device and the leg to sandwich the device between the leg and the wrap.

DESCRIPTION OF THE PREFERRED EMBODIMENT

Figure 1:
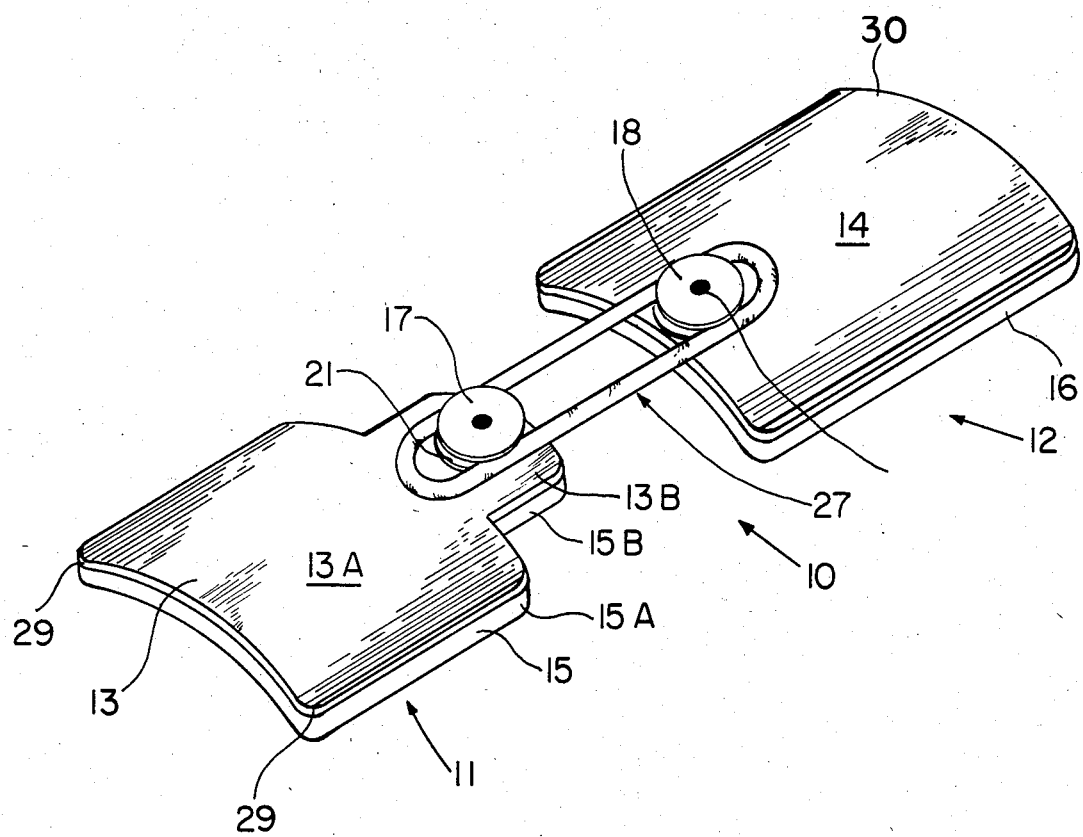
FIG. 1 is a perspective view of the first embodiment of the device of this invention.

Turning now to FIG. 1 of the drawings, a top perspective view of the device of this invention is seen. Device 10 includes a first main portion 11 seen on the left of the figure and a second main portion 12 seen in the right of the figure. The first main portion 11 comprises a convex arcuate plate which includes a generally rectangular first section 13A when viewed in top plan, and an extension second section 13B of a width less than the width of said first section. The second section extends in the direction of said second main portion 12. This second main portion is also a convex arcuate plate of a generally rectangular configuration in top plan and which is designated 14. The degree of convexity of the plates 13 and 14 is the same and can range from about 6/16" to about 10/16" in elevation. Each of said plates 13 and 14 preferably includes chamfered corners 29 and rounded edges 30 to prevent injury to the wearer of the device.

Figure 2:
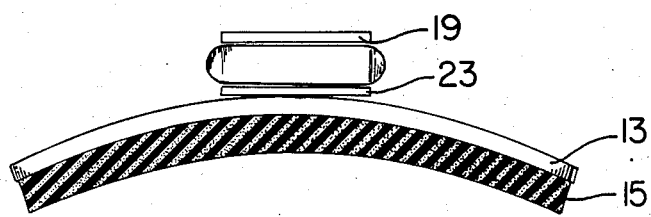
FIG. 2 is a right side elevation thereof.

Disposed on the underside of each of said arcuate plates, curvature extending across the width of the device 10, i.e., normal to the longitudinal axis of the device 10, is a sponge rubber pad, designated 15 and 16. Pad 15 is configured in two parts 15A and 15B. These pads conform to the exterior dimensions of the pair of plates. As is seen in FIG. 2, the pads follow the convexity of the plate such that viewed from the underside, a concave recess is seen in the rubber. Latex or polyurethane or other conventional rubber padding may be employed. Pads 15 and 16 may be secured to the underside of the plates 13 and 14 by any conventional adhesive known in the art.

Figure 4:
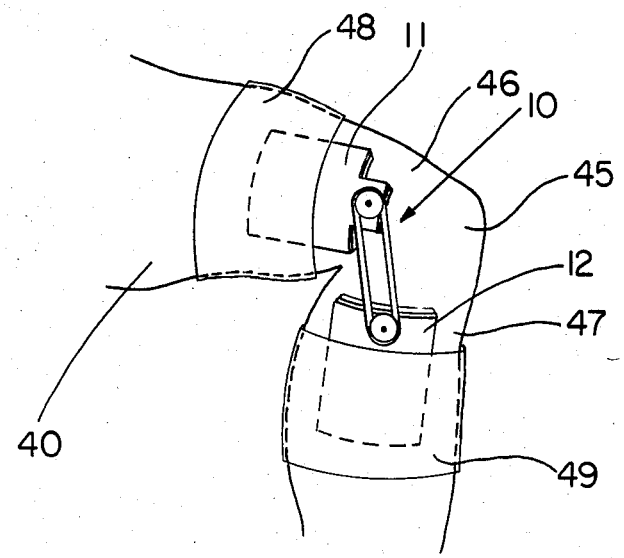
FIG. 4 is a perspective view of this embodiment of the knee brace of this invention positioned in place at the knee area of the intended recipient.

Mounted on the top surface of each of said plates 13 and 14 at the ends proximal each of the plates is a pulley. The pulley on section 13B is designated 17 while the one mounted on plate 14 is designated 18. Each pulley is mounted to the plate by conventional means such as rivet 20. Encircling the fixed sheaves 21 of said pulleys and carried by same, is a non-resilient endless belt 27. This belt is adapted to permit the sheaves to ride upon same and to permit rotation of the sheaves relative to the belt 27 during movement of the wearer's leg as illustrated in FIG. 4. Preferably, this belt is fashioned of rigid rod such as of steel or aluminum, or any other material that permits the motion described above, and which upon the application of pressure (see arrow 34) upon the plates 13 and/or 14 will bind up to prevent further movement of the pulleys 17,18 relative to the belt 27. Thus if a belt is used, it should have adequate thickness to permit the required binding effect to transpire upon the application of force against the plates which causes the plate to move away from the force whereby the sheave is cocked angularly from its relaxed normal position relative to the belt at which time the locking effect transpires. Upon the release of this force, the plate returns to its relaxed position and the sheave regains its normal position and the belt or tube is merely carried by the sheave.

The construction just described and the phenomenon of the operation of the instant device to prevent injury is also ascertainable from FIG. 2 wherein the upper and lower flanges 19 and 23 of the pulleys are seen, as well as FIG. 4 which will be described below.

Figure 3:
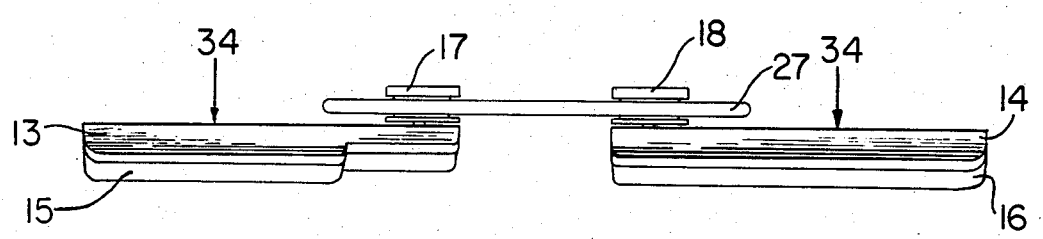
FIG. 3 is a front elevational view of the device of this invention.

In FIG. 3 an elevational view, the curvature of the plates 13 and 14 is readily seen, as is the following of the convexity of said plates by the pads 15 and 16.

Figure 5:
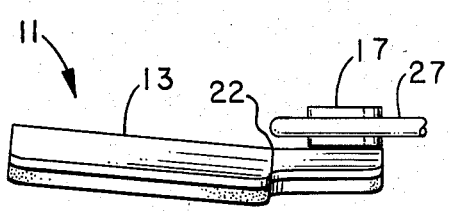
FIG. 5 is a view based upon FIG. 1 showing a variant of the embodiment of said Figure.

In FIG. 5, wherein like numbers refer to like parts a variant of the embodiment of FIG. 1 is shown. Here, the connecting link 27 is shown cutaway, because the portion of the variant, namely 12, that is secured below the knee is the same as in FIG. 1. The difference between the embodiment of FIG. 1 and that of FIG. 5 is that the variant of FIG. 5 is canted upwardly along crease 22 which forms a more distinct line of separation between 13A and 13B. In some players, with unusually wide thighs this crease 20 transverse to the length or long dimension of the device renders the application of the device more comfortable for the wearer.

In FIG. 4 the wearing of the first embodiment of the instant device on a person's leg 40 is illustrated. First portion 11 is rotated 90 degrees relative to said second main portion 12 and applied as by bandage 48 to the lateral area 46 above the patella 45 of the wearer. Second main portion 12 is held tightly against the outside of the area 47 below the patella by bandage 49. These are conventional bandages used by football players and known in the trade as Ace bandages. Other securing means known to the art may be used equally as well.

In the second embodiment of the device, instead of a sponge rubber pad on the underside of each of the metal plates, a laminate of neoprene rubber and velour fabric is secured in place. This laminate as show in FIG. 6 can be anywhere from 24 to 30 inches long.

Figure 6:
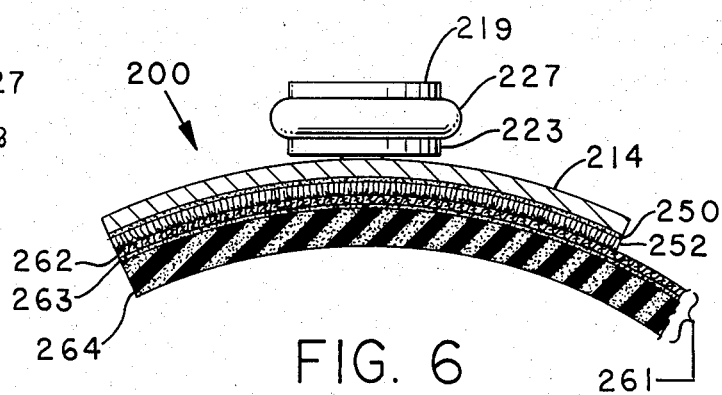
FIG. 6 is a cutaway diagrammatic elevational view of a second embodiment of the instant device.

We turn now to FIG. 6, which is a close-up end view, which diagrammatically illustrates a portion of the second embodiment, and which is similar to the view seen in FIG. 2 but from the opposite end of the device. In this second embodiment 200, elements 219, 227, 223, 214 are all the same as their two digit counterparts 19, 27, 23, and 14 and in view of this no further discussion is needed on these elements. The other metallic elements of the second embodiment 200 would also be of similar configuration as those shown in FIGS. 1–5 and would relate to each other in like manner. FIG. 6 therefore is seen to be a cutaway view, the outer edges of the layers being cutoff for ease of both drawing of the figure and for understanding the content thereof.

Figure 7:
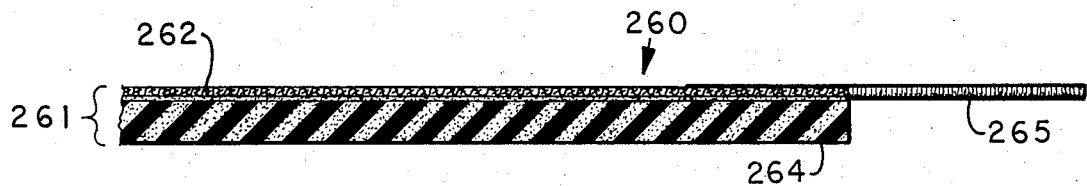
FIG. 7 is a diagrammatic close-up view of a portion of the second embodiment of this invention.

Thus the underside of metal plate 213 is covered with an adhesive layer 250 to which is secured a layer of male Velcro, i.e. the hook portion, 252. Secured to said hook layer 252 is wrap 260 which is a laminate 261 comprised of a layer of velour-like fabric 262 which is adapted to be engageable by the male Velcro. Adhesed by adhesive layer 263 to the underside of said velour-like layer is a layer of neoprene rubber 264. In FIG. 7 a portion of wrap 260 is seen. As mentioned above, it can be 2 to 2.5 feet long. Said wrap 260 includes the laminate 261 previously described, and a terminal portion at one end of a sheet of male Velcro, 265 which is stitched to said laminate 261. Velcro is a trademark of Velcro AG of Friboorg Switzerland for its fabric closure system, which is readily available in the marketplace.

Figure 8:
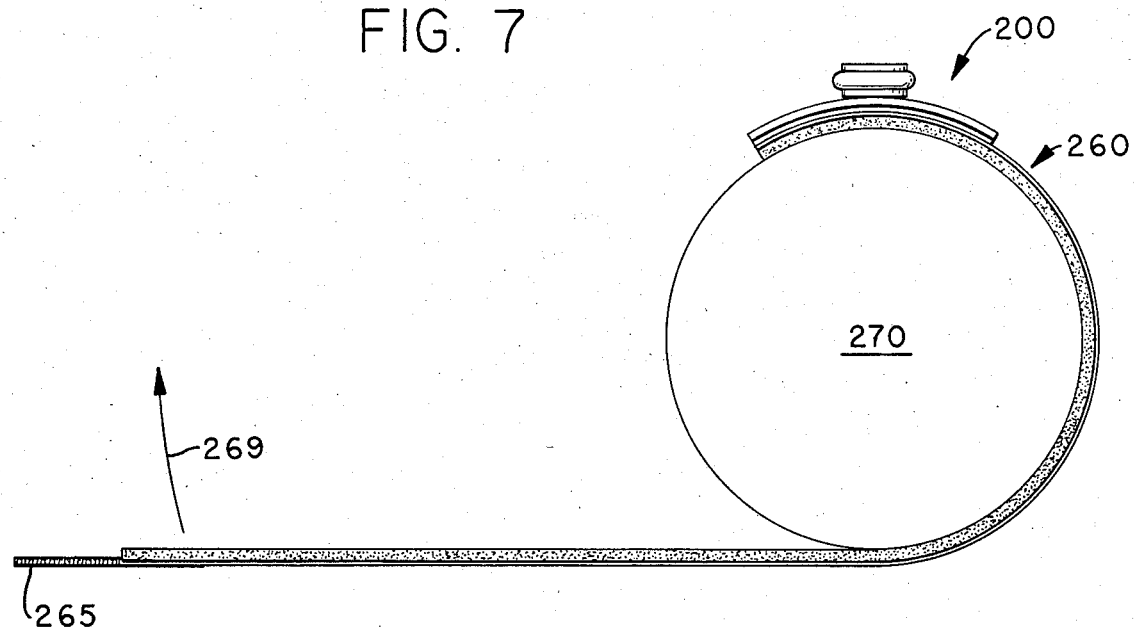
FIGS. 8 and 9 are diagrammatic views showing the use of the second embodiment of the instant invention.
Figure 9:
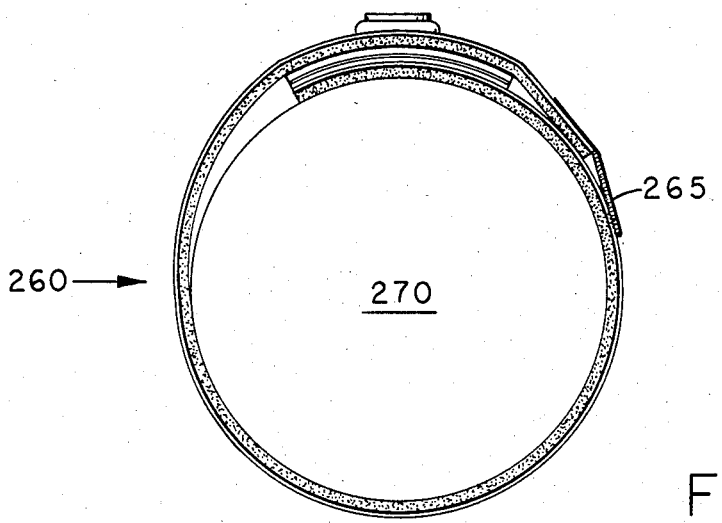

In use, the wrap 260 is wrapped around the leg, 270, and over the metal plate 213 to bind it tightly to the thigh, and then the terminal portion 265 is removably secured to the laminate to ensure that the device is bound tightly to the leg. Reference is made to FIGS. 8 and 9.

In FIG. 8, the device 200 is seen from an end view placed upon the thigh of a player. The wrap 260 is dangling from beneath the first Velcro layer 252 on the underside of the metal plate 213. When the wrap is rotated around and over the top of the metal plate 213, per arrow 269, as shown in FIG. 9, and the terminal portion Velcro strip 265 also designated the second Velcro portion, is wrapped around and permitted to grip the wrap itself, then a tight binding placement of the device 200 and the wrap 260 on the thigh 270 will take place.

In the typical construction of the instant device, ⅛th inch thick aluminum plates 3½×4 inches for section 13A and 1½×4 inches for 13B and 5 by 4 inches for plate 14 are employed. The sheaves which typically stand 1 inch tall in conjunction with the endless belt 27 help protect the lateral side of the patella from direct blows. The metallic parts of the second embodiment being the same as in the first embodiment would also be made of the same materials and, i.e. aluminum or perhaps polycarbonate plastic, and would be of the same dimensions. While the rubber portion of the wrap is preferably neoprene, any soft rubber that will not irritate the skin may be employed. Wraps as previously described with the depending sheet of male Velcro are available in the marketplace, but for a different purpose, are sold under the tradename Turtle Hydes by Dricast Orthopedics, Inc.

Translational motion of the stabilizer is limited by the locking of the belt 27 against flanges 19 and 23 of the pulleys. Use of the present invention makes it possible to have convenient, effective means for stabilizing and supporting the knee joint to thereby eliminate discomfort or possible injury or re-injury to the knee joint. Sheave lock arrangement is a novel feature among knee braces when tested by inexperienced high school football players, who wore the described knee stabilizer in game conditions and practice. No injury of the knee occurred under those severe stress conditions of use. Each player was able to perform his prescribed duties of the game.

Since certain changes may be made in the above apparatus without departing from the scope of the invention involved herein, it is intended that all matter contained in the above description and shown in the accompanying drawings shall be interpreted as illustrative and not in a limiting sense.

I claim:

1. A knee stabilizer for the support and protection of the knee joint which comprises:
a pair of first and second plates spaced one from the other, the first of which plates includes an arcuate shaped extension portion of a width less the width of said first plate, the extension portion extending axially in the direction toward said second plate,
said second plate and the extension portion of said first plate each have a fixed sheave pulley mounted on the top surfaces thereof, with a rigid endless belt encircling said pulleys wherein the endless belt is a non-resilient rigid tubing means adapted to lock against at least one of said pulleys to thereby lock said belt into a fixed position, upon the application of force to one of said plates, and released from said fixed position upon the release of such force.

2. In the device of claim 1 wherein the pulleys lie along the central longitudinal axis of the device.

3. In the stabilizer of claim 1 wherein padding is disposed on the underside of said plates.

4. In the device of claim 3 wherein the padding is a foam selected from the group consisting of latex rubber and polyurethane foam.

5. In the device of claim 1 wherein the plates and pulleys are made of aluminum.

6. In the device of claim 1 wherein the endless belt is an elliptical solid link.

7. In the device of claim 1 wherein the plates are arcuate convex shaped.

8. In the device of claim 7 wherein the plates are padded on the underside, and the padding conforms to the shape of the plates.

9. In the device of claim 2 wherein a first layer of male Velcro is adhesed to the underside of said plates.

10. In the device of claim 9 wherein releaseably secured to said first Velcro layer is a wrap comprising a laminate of velour-like fabric adhesed to a co-extensive layer of rubber, and having a depending terminal portion of a second male Velcro sheet.

11. In the device of claim 2 wherein a first layer of male Velcro is adhesed to the underside of said plates, and further wherein releaseably secured to said first Velcro layer is a wrap comprising a laminate of velour-like fabric adhesed to a co-extensive layer of rubber, and having a depending terminal portion of a second male Velcro sheet.

* * * * *